US00PP25260P2

(12) United States Plant Patent
Schaber

(10) Patent No.: US PP25,260 P2
(45) Date of Patent: Jan. 27, 2015

(54) GERANIUM PLANT NAMED 'OGLGER7023'

(50) Latin Name: *Pelargonium peltatum*
Varietal Denomination: Oglger7023

(71) Applicant: Margaret Schaber, Encinitas, CA (US)

(72) Inventor: Margaret Schaber, Encinitas, CA (US)

(73) Assignee: Ecke Ranch B.V., De Lier (NL)

( * ) Notice: Subject to any disclaimer, the term of this patent is extended or adjusted under 35 U.S.C. 154(b) by 85 days.

(21) Appl. No.: 13/815,476

(22) Filed: Mar. 5, 2013

(51) Int. Cl.
*A01H 5/00* (2006.01)

(52) U.S. Cl.
USPC ..... Plt./332

(58) Field of Classification Search
USPC ..... Plt./332
See application file for complete search history.

*Primary Examiner* — Annette Para
(74) *Attorney, Agent, or Firm* — C. A. Whealy

(57) ABSTRACT

A new and distinct cultivar of Ivy Geranium plant named 'Oglger7023', characterized by its upright to outwardly spreading and uniformly mounding to trailing plant habit; vigorous growth habit; freely branching habit; medium green-colored leaves with a discernible zonation pattern; freely flowering habit; and bright red purple-colored flowers arranged in umbels held above and beyond the foliar plane on strong peduncles.

1 Drawing Sheet

Botanical designation: *Pelargonium peltatum.*
Cultivar denomination: 'OGLGER7023'.

BACKGROUND OF THE INVENTION

The present invention relates to a new and distinct cultivar of Ivy Geranium plant, botanically known as *Pelargonium peltatum*, and hereinafter referred to by the name 'Oglger7023'.

The new Ivy Geranium plant is a product of a planned breeding program conducted by the Inventor in Lompoc, Calif. The objective of the breeding program is to create new upright and uniform Ivy Geranium plants with attractive leaf and flower coloration.

The new Ivy Geranium plant originated from a cross-pollination made by the Inventor in June, 2005 in Lompoc, Calif. of *Pelargonium peltatum* 'Free Derose', disclosed in U.S. Plant Pat. No. 18,043, as the female, or seed, parent with *Pelargonium peltatum* 'Global Rose', disclosed in U.S. Plant Pat. No. 10,514, as the male, or pollen, parent. The new Ivy Geranium plant was discovered and selected by the Inventor as a single flowering plant from within the progeny of the stated cross-pollination in a controlled greenhouse environment in Lompoc, Calif. on Mar. 1, 2006.

Asexual reproduction of the new Ivy Geranium plant by vegetative cuttings in a controlled greenhouse environment in Connellsville, Pa. since September, 2006, has shown that the unique features of this new Ivy Geranium plant are stable and reproduced true to type in successive generations.

SUMMARY OF THE INVENTION

Plants of the new Ivy Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Oglger7023'.

These characteristics in combination distinguish 'Oglger7023' as a new and distinct Ivy Geranium plant:

1. Upright to outwardly spreading and uniformly mounding to trailing plant habit.
2. Vigorous growth habit.
3. Freely branching habit.
4. Medium green-colored leaves with a discernible zonation pattern.
5. Freely flowering habit.
6. Bright red purple-colored flowers arranged in umbels held above and beyond the foliar plane on strong peduncles.

Plants of the new Ivy Geranium differ primarily from plants of the female parent, 'Free Derose', in flower form as flowers of plants of the new Ivy Geranium have more petals than flowers of plants of 'Free Derose'.

Plants of the new Ivy Geranium differ primarily from plants of the male parent, 'Global Rose', in flower color as plants of 'Global Rose' have lavender rose-colored flowers.

Plants of the new Ivy Geranium can be compared to plants of *Pelargonium peltatum* 'Global Soft Pink', disclosed in U.S. Plant Pat. No. 14,085. In side-by-side comparisons conducted in Encinitas, Calif., plants of the new Ivy Geranium differed primarily from plants of 'Global Soft Pink' in leaf and flower color as plants of 'Global Soft Pink' had light green-colored leaves and soft pink-colored flowers.

BRIEF DESCRIPTION OF THE PHOTOGRAPHS

The accompanying colored photographs illustrate the overall appearance of the new Ivy Geranium plant showing the colors as true as it is reasonably possible to obtain in colored reproductions of this type. Colors in the photographs may differ slightly from the color values cited in the detailed botanical description which accurately describe the colors of the new Ivy Geranium plant.

The photograph at the bottom of the sheet comprises a side perspective view of a typical flowering plant of 'Oglger7023' grown in a container.

The photograph at the top of the sheet is a close-up view of a typical flowering plant of 'Oglger7023'.

DETAILED BOTANICAL DESCRIPTION

The aforementioned photographs and following observations, measurements and values describe plants grown during the early spring in 16.5-cm containers in a polyethylene-covered greenhouse in Encinitas, Calif. and under cultural conditions which closely approximate Ivy Geranium commercial production. During the production of the plants, day temperatures averaged 27° C., night temperatures averaged 18° C. and light levels averaged 4,000 foot-candles. Plants were 17 weeks old when the photographs and the description were taken. In the detailed description, color references are made to The Royal Horticultural Society Colour Chart, 2007 Edition, except where general terms of ordinary dictionary significance are used.

Botanical classification: *Pelargonium peltatum* 'Oglger7023'.

Parentage:

*Female, or seed, parent.*—*Pelargonium peltatum* 'Free Derose', disclosed in U.S. Plant Pat. No. 18,043.

*Male or pollen parent.*—*Pelargonium peltatum* 'Global Rose', disclosed in U.S. Plant Pat. No. 10,514.

Propagation:

*Type*.—By vegetative cuttings.

*Time to initiate roots, summer*.—About ten days at temperatures about 20° C.

*Time to initiate roots, winter*.—About two weeks at temperatures about of 16° C.

*Time to produce a rooted young plant, summer*.—About four weeks at temperatures about 20° C.

*Time to produce a rooted young plant, winter*.—About four weeks at temperatures about 16° C.

*Root description*.—Fine, fibrous; white in color.

*Rooting habit*.—Freely branching; dense.

Plant description:

*Plant and growth habit*.—Upright, outwardly spreading and uniformly mounding to trailing plant habit; vigorous growth habit.

*Branching habit*.—Freely branching habit with about five to six primary lateral branches developing per plant, each primary lateral branch with secondary lateral branches; dense and bushy appearance; pinching enhances lateral branch development.

*Plant height, to top of umbels*.—About 20 cm.

*Plant height, to top of foliar plane*.—About 17.5 cm.

*Plant diameter* (*spread*).—About 21 cm by 24 cm.

*Lateral branches*.—Length: About 19 cm. Diameter: About 3 mm. Internode length: About 3.7 cm. Texture: Pubescent; scattered. Strength: Strong. Aspect: Initially upright, then falling over with development. Color: Close to 146C.

Foliage description:

*Arrangement*.—Opposite; simple.

*Length*.—About 5.8 cm.

*Width*.—About 6.5 cm.

*Shape*.—Oval to nearly round; palmately lobed.

*Apex*.—Broadly acute.

*Base*.—Cordate to auriculate.

*Margin*.—Entire with five to seven rounded lobes.

*Venation pattern*.—Palmate, reticulate.

*Texture, upper surface*.—Pubescent, scattered; coarse.

*Texture, lower surface*.—Pubescent, minute.

*Color*.—Developing leaves, upper surface: Close to 137B. Developing leaves, lower surface: Close to 146B. Fully expanded leaves, upper surface: Close to 146A; venation, close to 146B. Zonation pattern: Location: About 6 mm from upper leaf surface margin. Width: About 2 cm. Color: Close to 166A. Fully expanded leaves, lower surface: Close to 146B; venation, close to 146B.

*Petiole*.—Length: About 3 cm. Diameter: About 2 mm. Texture, upper and lower surfaces: Pubescent, minute. Color, upper and lower surfaces: Close to 146B.

Flower description:

*Flower arrangement*.—Round double flowers arranged in flattened hemispherical umbels arising from apical leaf axils; umbels displayed above and beyond the foliar plane on strong peduncles; umbels mostly upright and flowers face upright or outwardly.

*Fragrance*.—None detected.

*Quantity of flowers*.—Freely flowering habit; about ten to twelve flowers per umbel and about 18 to 22 umbels per plant at one time.

*Flowering season*.—In California, flowering is continuous during the spring and summer.

*Flower longevity*.—Individual flowers last about five to seven days on the plant; flowers persistent.

*Umbel height*.—About 4.4 cm.

*Umbel diameter*.—About 7 cm.

*Flower diameter*.—About 4 cm to 4.4 cm.

*Flower depth* (*height*).—About 2.3 cm.

*Flower buds*.—Length: About 1.6 cm. Diameter: About 8 mm. Shape: Oval. Color: Close to N8OB to N80D.

*Petals*.—Quantity per flower and arrangement: Typically 20 arranged in three to four whorls. Length: About 2.5 cm. Width: About 1.6 cm. Shape: Obovate to elliptical. Apex: Rounded. Base: Acute. Margin: Entire. Texture, upper and lower surfaces: Smooth, glabrous; velvety. Color: When opening, upper surface: Close to N74A. When opening, lower surface: Close to N78B to N78D. Fully opened, upper surface: Close to 67B; venation, close to 67B; color does not fade with development. Fully opened, lower surface: Close to 67C; venation, close to 67C; color does not fade with development.

*Petaloids*.—Quantity per flower and arrangement: Typically about ten central to the whorls of petals. Length: Variable, about 1.2 cm to 1.6 cm. Width: Variable, about 2 mm to 5 mm. Shape: Variable, narrowly obovate to lanceolate. Apex: Rounded. Base: Acute. Margin: Entire. Texture, upper and lower surfaces: Smooth, glabrous; velvety. Color: When opening, upper surface: Brighter than N74A. When opening, lower surface: Close to 67C. Fully opened, upper surface: Close to N74A. Fully opened, lower surface: Close to N74C.

*Sepals*.—Quantity per flower: Typically five arranged in a single whorl. Length: About 1.6 cm. Width: About 3 mm. Shape: Narrowly elliptical. Apex: Acuminate. Base: Truncate. Margin: Entire. Texture, upper surface: Smooth, glabrous. Texture, lower surface: Pubescent, minute. Color, upper surface: Close to 148B. Color, lower surface: Close to 148C.

*Peduncle* (*umbel stem*).—Length: About 8.8 cm. Diameter: About 2.5 mm. Angle: About 45° from stem axis. Strength: Strong. Texture: Pubescent; minute. Color: Close to 146B.

*Pedicel* (*individual flower stem*).—Length: About 2.2 cm. Diameter: About 2 mm. Angle: About 55° from peduncle axis. Strength: Strong. Texture: Pubescent; minute. Color: Close to 146B.

*Reproductive organs*.—Androecium: Stamen quantity per flower: About three to ten; occasionally modified into petaloids. Filament length: About 8 mm. Filament color: Close to NN155D tinted with close to 73C. Anther length: About 2.5 mm. Anther shape: Oblong. Anther color: Close to 70B. Pollen amount: Scarce. Pollen color: Close to 178B. Gynoecium: Pistil quantity per flower: One. Pistil length: About 1.1 cm. Stigma shape: Five-parted, star-shaped; recurved. Stigma color: Close to N77A. Style length: About 4 mm. Style color: Close to 157C. Ovary color: Close to 195D.

*Seeds and fruits*.—Seed and fruit development have not been observed on plants of the new Ivy Geranium.

Disease & pest resistance: Plants of the new Ivy Geranium have not been observed to be resistant to pathogens and pests common to Ivy Geranium plants.

Temperature tolerance: Plants of the new Ivy Geranium have been observed to tolerate temperatures ranging from about 1° C. to about 35° C.

It is claimed:

1. A new and distinct Ivy Geranium plant named 'Oglger7023' as illustrated and described.

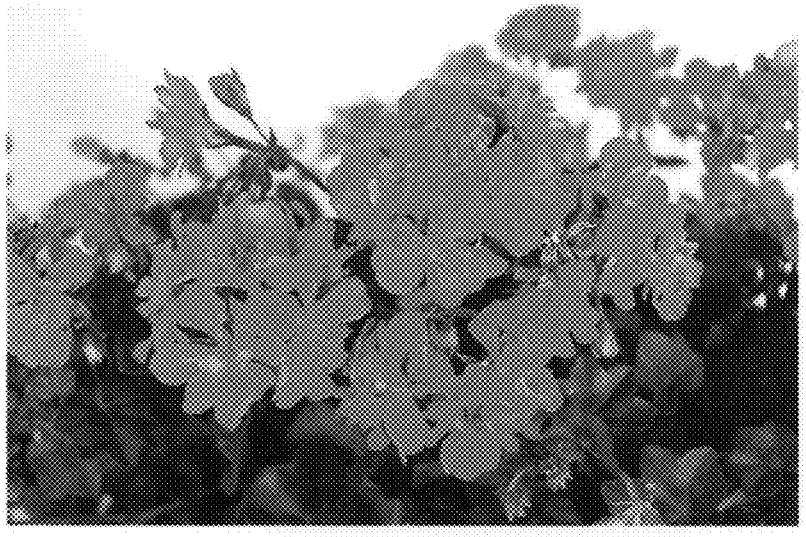
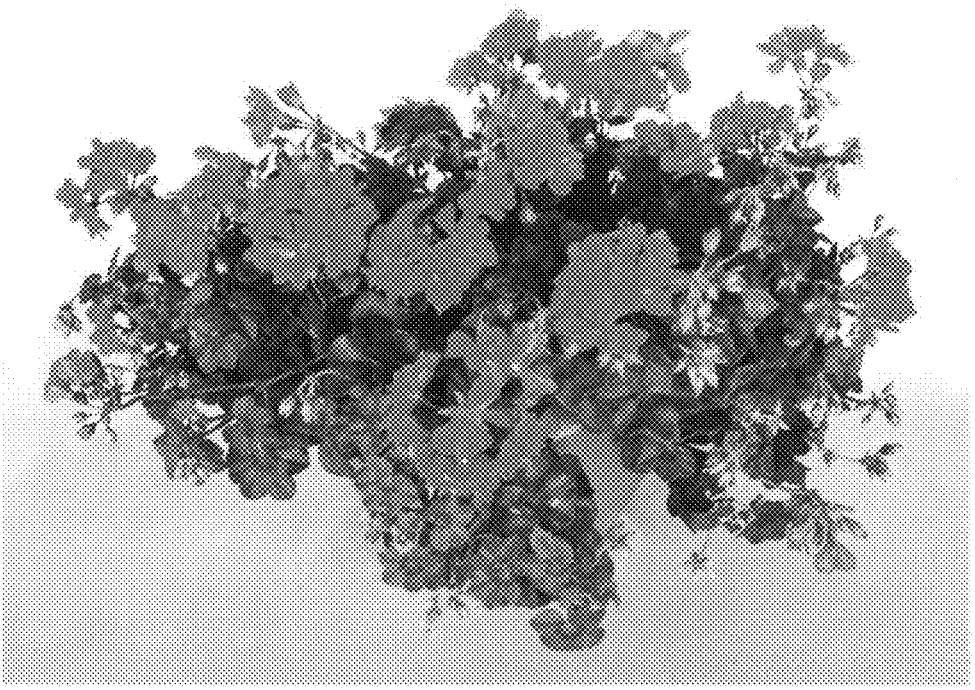

* * * * *